United States Patent
Yamada et al.

(10) Patent No.: US 6,570,035 B2
(45) Date of Patent: May 27, 2003

(54) PROCESS FOR PRODUCING PIVALOYL-ACETIC ACID ESTER

(75) Inventors: Shinya Yamada, Kanagawa (JP); Yoshiki Okeda, Kanagawa (JP); Toshimitsu Hagiwara, Kanagawa (JP); Akio Tachikawa, Kanagawa (JP); Kouji Ishiguro, Kanagawa (JP); Shunichi Harada, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/759,134

(22) Filed: Jan. 16, 2001

(65) Prior Publication Data

US 2001/0011141 A1 Aug. 2, 2001

(30) Foreign Application Priority Data

Jan. 14, 2000 (JP) ........................................ 2000-005144

(51) Int. Cl.[7] .............................................. C07C 69/66
(52) U.S. Cl. ...................................................... 560/174
(58) Field of Search ......................................... 560/174

(56) References Cited

U.S. PATENT DOCUMENTS 5,144,057 A * 9/1992 Eyer ............................ 560/51

FOREIGN PATENT DOCUMENTS

JP  10-25269  * 1/1998  ......... C07C/69/716

OTHER PUBLICATIONS

David L. Kuo, "Magnesium Chloride Catalysed Acylation Reaction", Tetrahedron, vol. 48 (1992), pp9233–9236.*
XP–002166182—Michael W. Rathke et al., Procedures for the Acylation of Diethyl Malonate and Ethyl Acetoacetate with Acid Chlorides Using Tertiary Amine Bases and Magnesium Chloride, J.Org. Chem. 1985, vol. 50, pp. 2622–2624.

* cited by examiner

Primary Examiner—Ceila Chang
Assistant Examiner—Taylor V. Oh
(74) Attorney, Agent, or Firm—Sughrue Mion, PLLC

(57) ABSTRACT

A process for producing a pivaloylacetic acid ester comprises reacting pivaloyl chloride with an acetoacetic acid ester of an alkyl group having 1 to 4 carbon atoms in the presence of at least one nitrogen-containing basic compound (a) selected from among pyridine compounds, N,N-dialkylanilines and imidazole compounds and from 0.01 to 0.5 mole equivalent, based on the pivaloyl chloride, of a magnesium compound (b) to thereby prepare a pivaloylacetoacetic acid ester and then alcholyzing or alkali-hydrolyzing the pivaloylacetoacetic acid ester to thereby give a pivaloylacetic acid ester having a high purity at a low cost.

7 Claims, No Drawings

PROCESS FOR PRODUCING PIVALOYL-ACETIC ACID ESTER

FIELD OF THE INVENTION

This invention relates to a process for producing a pivaloylacetic acid ester which is useful as a synthetic intermediate of, for example, photographic photosensitive materials.

BACKGROUND OF THE INVENTION

There have been known a number of processes for producing aliphatic β-ketoesters. Among these processes, cross-Claisen condensation described in, for example, C. R. Hauser et al., Organic Reactions, 1, 266 (1942) is known as a process for producing a pivaloylacetic acid ester. Although this process has an advantage that the production can be carried out by using a relatively inexpensive pivalic acid ester and an acetic acid ester as the starting materials, it is required therein to use at least one equivalent of a relatively expensive strong base (for example, sodium hydride). Therefore, this process is not always advantageous from an economical viewpoint.

Also, a process for producing a pivaloylacetic acid ester by reacting pinacolone with a carbonic acid diester at a stoichiometric ratio in the presence of an excessive amount of a metal alcholate is described in, for example, WO9855438A1, JP-A-9-110793, JP-A-9-40612, JP-A-7-215915, JP-A-6-279363, JP-A-6-279362, JP-A-6-271504, German Patent No. 2945604, German Patent No. 2412784, JP-A-6-279362 and JP-A-6-279363 (the term "JP-A" as used herein means an "unexamined published Japanese patent application"). Also, there is known a process for producing a pivaloylacetic acid diester by reacting pinacolone with an oxalic acid diester (JP-B-62-47170, JP-B-63-12464, German Patent No. 2945604, JP-A-8-27065, European Patent No. 693473; the term "JP-B" as used herein means an "examined Japanese patent publication"). However, these processes are not economically advantageous too, since it is required therein to use expensive solvents or relatively expensive pinacolone.

Furthermore, there are known a process for producing a pivaloylacetic acid ester by reacting pivaloyl chloride with an acetoacetic acid ester in the presence of magnesium hydroxide (JP-A-10-25269) and a process for producing a pivaloylacetic acid ester by reacting pivaloyl chloride with an acetoacetic acid ester in the presence of a magnesium alkoxide (East German Patent DD235636A1) However, these processes are not advantageous from both of the viewpoints of economy and operation, since the acetoacetic acid ester should be used in a large amount and, moreover, magnesium hydroxide should be used at least 50% by mol (being equivalent or more) based on the pivaloyl chloride. In addition, these processes suffer from an additional problem of the formation of much wastes.

Furthermore, there is known a process for producing a pivaloylacetic acid ester by reacting magnesium enolate of an acetoacetic acid ester with pivaloyl chloride in the presence of a tertiary amine and then deacetylating the resulting product (JP-A-4-264054, European Patent No. 481395A2). However, this process suffers from a problem that a magnesium compound is used in a stoichiometric amount or more and thus a large amount of magnesium waste is formed. In addition, it is stated in JP-A-10-25269 that no pivaloylacetic acid ester can be obtained by this process.

Pivaloylacetic acid esters are important starting compounds for producing photographic photosensitive materials in particular, yellow couplers to be used as photographic photosensitive materials. With the recent cost reduction in photographic photosensitive materials, it has been required to establish a process for economically producing pivaloylacetic acid esters. At the same time, pivaloylacetic acid esters to be used as the starting compounds for producing yellow couplers employed as photographic photosensitive materials should have high purity. However, pivaloylacetic acid esters produced by the conventional methods as described above by, for example, reacting an acetoacetic acid ester with an equimolar amount of magnesium methoxide and reacting the thus obtained magnesium enolate of the acetoacetic acid ester with pivaloyl chloride followed by alcoholysis or hydrolysis generally have only insufficient purity and, therefore, cannot be used in yellow couplers as photographic photosensitive materials.

M. W. Rathke et al. reported a process for synthesizing ethyl pivaloylacetoacetate, which is a precursor of ethyl pivaloylacetate, by reacting pivaloyl chloride with ethyl acetoacetate in the presence of anhydrous magnesium chloride in an equimolar amount to the pivaloyl chloride and twice by mole as much pyridine. However, this method of Rathke et al. is not economically advantageous, since expensive anhydrous magnesium chloride should be used in the equimolar amount to pivaloyl chloride. In this process, moreover, magnesium chloride employed in a large amount is not dissolved in a solvent, which makes stirring difficult and worsens the operating characteristics. In addition, a large amount of magnesium chloride remains as a waste after the completion of the reaction, which brings about a problem of environmental pollution and makes it necessary to carry out troublesome operations for treating the waste. In case where a pivaloylacetic acid ester is produced by preparing a pivaloylacetoacetic acid ester and then alcoholyzing the same in accordance with the method of Rathke et al., furthermore, the target pivaloylacetic acid ester cannot be always obtained at a high yield.

SUMMARY OF THE INVENTION

An object of the invention is to provide a process for producing a highly pure pivaloylacetic acid ester which is efficiently usable in, for example, a photographic photosensitive material at a low cost while achieving favorable operating characteristics.

Another object of the invention is to provide a process for producing a highly pure pivaloylacetic acid ester at a high yield and a high productivity.

To achieve the objects as described above, the inventors have conducted intensive studies. As a result, they have found out that in case of producing a pivaloylacetic acid ester by reacting pivaloyl chloride with an acetoacetic acid ester and then alcoholyzing or alkali-hydrolyzing the thus obtained pivaloylacetoacetic acid ester, a pivaloylacetic acid ester, which has a high purity and is little contaminated by by-products and, therefore, usable as a starting material for producing a yellow coupler employed as a photographic photosensitive material merely by distilling, can be obtained by reacting pivaloyl chloride with an acetoacetic acid ester in the presence of an aromatic nitrogen-containing basic compound such as a pyridine derivative and a small amount (0.5 mole equivalent or less based on the pivaloyl chloride) of a magnesium compound. The inventors have further found out that, since a magnesium compound is used only in a small amount (0.5 mole equivalent or less), the magnesium compound can be easily dispersed in a reaction medium and thus favorable operating characteristics (for example, in stirring) can be achieved; and that only a small amount of the magnesium compound is discharged as a waste after the completion of the reaction and thus can be easily treated, which is desirable from the viewpoint of preventing environmental pollution too. The inventors have furthermore found out that the production cost of the pivaloylacetic acid ester can be lowered in this process, since a relatively expensive magnesium compound (for example, anhydrous magnesium chloride) is employed only in a small amount therein. Moreover, the inventors have found out that in case where anhydrous magnesium chloride and/or anhydrous magnesium bromide (in particular, anhydrous magnesium chloride) is used as the magnesium compound in this process, a highly pure pivaloylacetic acid ester can be obtained at an extremely high yield. The invention has been completed based on these findings.

Accordingly, the invention provides a process for producing a pivaloylacetic acid ester which comprises reacting pivaloyl chloride represented by the following chemical formula (I):

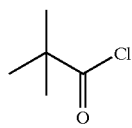

(I)

with an acetoacetic acid ester represented by the following general formula (II):

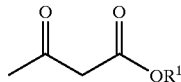

(II)

wherein $R^1$ represents an alkyl group having 1 to 4 carbon atoms; in the presence of at least one nitrogen-containing basic compound (a) selected from the group consisting of pyridine compounds, N,N-dialkylanilines and imidazole compounds and from 0.01 to 0.5 mole equivalent, based on the pivaloyl chloride, of a magnesium compound (b) to thereby prepare a pivaloylacetoacetic acid ester represented by the following general formula (III):

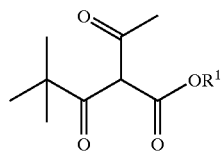

(III)

wherein $R^1$ represents an alkyl group having 1 to 4 carbon atoms; and then alcholyzing or alkali-hydrolyzing the pivaloylacetoacetic acid ester to thereby give a pivaloylacetic acid ester represented by the following general formula (IV):

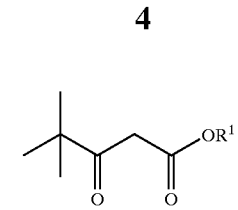

(IV)

wherein $R^1$ represents an alkyl group having 1 to 4 carbon atoms.

DETAILED DESCRIPTION OF THE INVENTION

Now, the invention will be described in greater detail.

The acetoacetic acid ester represented by the above-described general formula (II) (hereinafter sometimes referred to as the "acetoacetic acid ester (II)" to be reacted with pivaloyl chloride is an alkyl acetoacetate wherein $R^1$ forming the ester group is an alkyl group having from 1 to 4 carbon atoms. Particular examples of $R^1$ in the acetoacetic acid ester (II) include methyl, ethyl, n-propyl, isopropyl, n-butyl, sec-butyl, isobutyl and tert-butyl groups. $R^1$ may be an arbitrary alkyl group selected from among those cited above. Among all, it is preferable that the acetoacetic acid ester (II) is at least one of methyl acetoacetate wherein $R^1$ is a methyl group and ethyl acetoacetate wherein $R^1$ is an ethyl group from the viewpoints of, for example, there activity with pivaloyl chloride, the yield of the pivaloylacetic acid ester obtained finally, easiness in acquisition, cost and the reactivity of the obtained pivaloylacetic acid ester. It is still preferable to use methyl acetoacetate.

Taking the reactivity and the yield of the pivaloylacetic acid ester obtained finally into consideration, the pivaloyl chloride and the acetoacetic acid ester (II) are used preferably at a molar ratio of pivaloyl chloride: acetoacetic acid ester of from 2.0:1.0 to 1.0:2.0, still preferably from 1.6:1.0 to 1.0:1.6. By using less expensive one between pivaloyl chloride and the acetoacetic acid ester in a larger amount within the molar ratio range as specified above, the cost can be lowered.

The pivaloylacetoacetic acid ester represented by the above-described general formula (III) (hereinafter sometimes referred to as the "pivaloylacetoacetic acid ester (III)") is prepared by reacting pivaloyl chloride with the acetoacetic acid ester (II) in the presence of at least one nitrogen-containing basic compound (a) selected from among pyridine compounds, N,N-dialkylanilines and imidazole compounds and from 0.01 to 0.5 mole equivalent, based on the pivaloyl chloride, of a magnesium compound (b), as described above.

As the pyridine compound to be used as the nitrogen-containing basic compound (a), it is preferable to use pyridine compounds (pyridine or pyridine derivatives) represented by the following general formula (V):

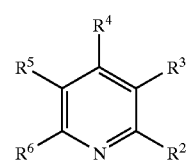

(V)

wherein $R^2$, $R^3$, $R^4$, $R^5$ and $R^6$ each independently represents a hydrogen atom, a methyl group or an ethyl group, or $R^2$ and $R^3$ or $R^3$ and $R^4$ may be bonded to each other to form a ring.

Examples of the pyridine compounds represented by the above-described general formula (V) (hereinafter sometimes referred to as the "pyridine compound (V)") include pyridine, α-picoline, β-picoline, γ-picoline, 2,6-lutidine, 2-ethylpyridine, 3-ethylpyridine, 4-ethylpyridine, quinoline and isoquinoline.

As the N,N-dialkylaniline to be used as the nitrogen-containing basic compound (a), it is preferable to use N,N-dialkylanilines represented by the following general formula (VI):

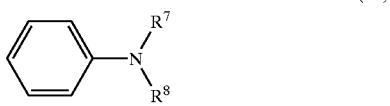

wherein $R^7$ and $R^8$ each independently represents an alkyl group having from 1 to 4 carbon atoms. Among all, dimethylaniline and/or diethylaniline are more preferable.

As the amidazole compound to be used as the nitrogen-containing basic compound (a), it is preferable to use imidazole compounds represented by the following general formula (VII):

wherein $R^9$ represents a hydrogen atom, a methyl group or an ethyl group.

In the invention, use can be made, as the nitrogen-containing basic compound (a), of one or more members selected from among the pyridine compounds, N,N-dialkylanilines and imidazole compounds as cited above. Among all, it is preferable in the invention to use at least one pyridine compound selected from among α-picoline, pyridine and 2,6-lutidine as the nitrogen-containing basic compound (a), since these compounds enable the production of a highly pure pivaloylacetic acid ester at a high yield and can be easily recovered owing to the low boiling point. In particular, it is still preferable to use α-picoline alone or α-picoline and one or more of other compounds cited as the nitrogen-containing basic compounds (a).

To obtain the target pivaloylacetic acid ester at a high yield, it is preferable to use the nitrogen-containing basic compound (a) in an amount of from 1.0 to 10.0 mole equivalents based on pivaloyl chloride (namely, from 1.0 to 10.0 mol per mol of pivaloyl chloride), still preferably from 1.5 to 2.5 mole equivalents.

As the magnesium compound (b), it is preferable to use an anhydrous magnesium compound. This is because the reaction between pivaloyl chloride and the acetoacetic acid ester (II) is frequently ceased or inhibited in case of using a moisture-containing magnesium compound.

Examples of the magnesium compound (b) to be used in the invention include anhydrous magnesium chloride, magnesium bromide, magnesium hydroxide, magnesium alkoxides (for example, magnesium methoxide, magnesium ethoxide), magnesium acetylacetonate, magnesium pivalate and magnesium compounds called Grignard reagents. It is preferable to use one or more anhydrous magnesium compounds selected from those cited above. Among all, it is preferable to use at least one of anhydrous magnesium chloride and anhydrous magnesium bromide (in particular, anhydrous magnesium chloride) as the magnesium compound (b), since these compounds contribute to the smooth progress of the reaction between pivaloyl chloride and the acetoacetic acid ester (II) even in a small amount and enable the acquisition of the target highly pure pivaloylacetic acid ester at a high yield. Moreover, these compounds can be easily obtained and remain relatively stable in the atmosphere.

It is necessary in the invention to use the magnesium compound (b) at a ratio of from 0.01. to 0.5 mole equivalent based on pivaloyl chloride (namely, from 0.01 to 0.5 mol per mol of pivaloyl chloride), preferably from 0.1 to 0.5 mole equivalent and still preferably from 0.2 to 0.5 mole equivalent.

When the magnesium compound (b) is used in an amount less than 0.01 mole equivalent, it takes a long time to complete the reaction between pivaloyl chloride and the acetoacetic acid ester (ii) to give the pivaloylacetic acid ester at a high yield, which results in a decrease in the productivity or an increase in the cost. When the magnesium compound (b) is used in an amount exceeding 0.5 mole equivalent, on the other hand, the yield of the target pivaloylacetic acid ester is lowered. In this case, moreover, the magnesium compound (b) is hardly dispersible in the reaction medium, which makes operations such as stirring difficult. Furthermore, a large amount of the magnesium compound (b) is discharged as a waste after the completion of the reaction and thus much labor, cost and time are needed for treating the waste.

For the quick and smooth progress of the reaction between pivaloyl chloride and the acetoacetic acid ester (II) in the presence of the nitrogen-containing basic compound (a) and the magnesium compound (b), it is preferable to carry out the reaction in an organic solvent. The organic solvent employed herein maybe an arbitrary one, so long as it is inert to pivaloyl chloride, the acetoacetic acid ester (II), the nitrogen-containing basic compound (a) and the magnesium compound (b). Examples thereof include aromatic hydrocarbons such as benzene, toluene, xylene and chlorobenzene, alkane halides such as methylene chloride, chloroform and dichloroethane, aliphatic hydrocarbons such as hexane and heptane, nitrites such as acetonitrile, proipionitrile, butyronitrile, valeronitrile and benzonitrile, and polar solvents such as tetrahydrofuran, methyl isobutyl ketone and methyl t-butyl ether. Either one of these organic solvents or a mixture of two or more thereof may be used. Among all, it is preferable to use aromatic hydrocarbons such as benzene, toluene and xylene or alkane halides such as methylene chloride, chloroform and dichloroethane. It is particularly preferable to use methylene chloride and/or toluene, since the acetoacetic acid ester can be prepared at a high yield thereby.

The amount of the organic solvent to be used herein is not particularly restricted. From the viewpoints of, for example, the smooth progress of the reaction, the easiness in the reaction operations (for example, stirring), the cost and the pot efficiency, it is generally favorable to use 25 to 550 ml (still preferably 80 to 280 ml) of the organic solvent per mol of the sum of pivaloyl chloride, the acetoacetic acid ester (II), the nitrogen-containing basic compound (a) and the magnesium compound (b).

The reaction between pivaloyl chloride and the acetoacetic acid ester (II) can be performed over a wide temperature range including room temperature. Considering, for example, the parity and yield of the target pivaloylacetic acid ester, prevention of the extension of the reaction time, the heat efficiency and the stirring efficiency, it is generally preferable that the reaction temperature ranges from 0 to 100° C., still preferably from 10 to 90° C. and still more preferably from 40 to 70° C. In case where the reaction temperature is excessively low, the reaction between pivaloyl chloride and the acetoacetic acid ester (II) cannot quickly proceed and thus it takes a long time for the formation of the pivaloylacetoacetic acid ester (III). In case where the reaction temperature is excessively high, on the other hand, the reaction time is shortened but much by-products are formed. Thus, there arise unfavorable results such that the yield and purity of the pivaloylacetoacetic acid ester (III) are lowered and, in its turn, the yield and purity of the target pivaloylacetic acid ester are lowered.

The pivaloylacetoacetic acid ester (III) obtained by the reaction between pivaloyl chloride and the acetoacetic acid ester (II) can be isolated by distilling under reduced pressure. However, it is unstable to heat and thus sometimes partly decomposed during the distillation. Accordingly, it is preferable that, after the completion of the reaction between pivaloyl chloride and the acetoacetic acid ester (II), the pivaloylacetoacetic acid ester (III) thus formed is not isolated from the reaction system but subjected, as in the reaction system, to alcoholysis or alkali-hydrolysis by adding an alcohol or an alkali to thereby form the target pivaloylacetic acid ester which is then recovered from the reaction system by distillation.

As the alcohol to be used in the alcoholysis of the pivaloylacetoacetic acid ester (III), it is preferable to employ an alcohol having 1 to 4 carbon atoms. Particular examples thereof include methanol, ethanol, n-propyl alcohol, isopropyl alcohol, n-butyl alcohol, sec-butyl alcohol, isobutyl alcohol and tert-butyl alcohol. Among all, it is preferable to use methanol and/or ethanol therefor.

In the alcoholysis, the alcohol is used at least in an equivalent amount to the pivaloylacetoacetic acid ester (III). Although the alcoholysis can be carried out over a wide temperature range including room temperature, the temperature preferably ranges from 30 to 70° C. in general.

The alcoholysis of the pivaloylacetoacetic acid ester (III) may be performed by directly adding the alcohol to the reaction system immediately after the completion of the preparation of the pivaloylacetoacetic acid ester (III). Alternatively, the alcohol may be added to the reaction system after removing the organic solvent, the nitrogen-containing basic compound (a) and/or the magnesium compound (b) from the reaction system by vacuum distillation or other methods after the completion of the preparation of the pivaloylacetoacetic acid ester (III).

As the alkali to be used in the hydrolysis of the pivaloylacetoacetic acid ester (III), it is preferable to use a dilute aqueous solution of an alkali. Particular examples thereof include 5 to 30% aqueous solutions of sodium hydroxide, potassium hydroxide, sodium carbonate and sodium hydrogencarbonate. It is preferable that the amount of the alkali to be used in the hydrolysis of the pivaloylacetoacetic acid ester (III) is regulated so as to not exceed twice by mole (calculated) as much as the pivaloylacetoacetic acid ester (III) Although the alkali-hydrolysis can be carried out over a wide temperature range including room temperature, the temperature preferably ranges from 20 to 70° C. in general.

The alkali-hydrolysis of the pivaloylacetoacetic acid ester (III) may be performed by directly adding the alkali to the reaction system immediately after the completion of the preparation of the pivaloylacetoacetic acid ester (III). Alternatively, the alkali may be added to the reaction system after removing the organic solvent, the nitrogen-containing basic compound (a) and/or the magnesium compound (b) from the reaction system by vacuum distillation or other methods after the completion of the preparation of the pivaloylacetoacetic acid ester (III).

The pivaloylacetic acid ester obtained by the alcoholysis or the alkali-hydrolysis as described above is recovered from the reaction system. Although the pivaloylacetic acid ester may be recovered from the reaction system by an arbitrary method without restriction, it is generally preferable to employ, for example, the vacuum distillation or the silica gel chromatography method therefor. In case of recovering the pivaloylacetic acid ester by vacuum distillation, it is preferable to control the temperature to 50 to 150° C. and the pressure to $1.0 \times 10^1$ to $7.0 \times 10^3$ Pa.

Because of having a high purity and being contaminated little by-products, the pivaloylacetic acid ester obtained by the process of the invention is efficiently usable merely after distillation as, for example, the starting compound for producing a yellow coupler which is a photographic photosensitive material.

EXAMPLES

Now, the invention will be described in greater detail by referring to the following Examples. However, it is to be understood that the invention is not construed as being limited thereto.

In the following Examples, the yield of each pivaloylacetic acid ester was measured by using a GC353 Gas Chromatography Apparatus (column: "NB-1") manufactured by GL Sciences Inc. which was operated under the following conditions; initial temperature: 80° C., temperature elevation rate; 5° C./min, injection temperature: 250° C., and detection temperature: 250° C.

Example 1

(1) 2.32 g (20.0 mmol) of methyl acetoacetate and 381 mg (4.00 mmol) of anhydrous magnesium chloride were suspended in 40 ml of a methylene chloride. Into the suspension thus obtained, 3.24 ml (40.0 mol) of pyridine was dropped at 0° C. After stirring for 10 minutes, 2.46 ml (20.0 mmol) of pivaloyl chloride was slowly dropped thereinto at the same temperature and the obtained mixture was reacted under stirring at 0° C. for 15 minutes and then at room temperature for 20 hours.

(2) To the reaction mixture obtained in (1), 2.56 g (80.0 mmol) of methanol was added and the obtained mixture was stirred at room temperature for 3 days thereby performing alcoholysis. Next, 1.50 g of heptadecane (an internal standard) was added and the yield of the thus for methyl pivaloylacetate (the yield based on the pivaloyl chloride serving as the starting material) was measured by gas chromatography. As a result, the yield was 70.9%, as shown in the following Table 1.

Example 2

Methyl pivaloylacetate was produced as in Example 1(1) but using 952.5 mg (10.0 mmol) of anhydrous magnesium chloride. Then the yield was measured by gas chromatography as in Example 1(2). Thus the yield of methyl pivaloylacetate (the yield based on the pivaloyl chloride) was 65.98, as shown in the following Table 1.

Comparative Example 1

Methyl pivaloylacetate was produced as in Example 1(1) but using 1905 mg (20.0 mmol) of anhydrous magnesium chloride. Then the yield was measured by gas chromatography as in Example 1(2). Thus the yield of methyl pivaloylacetate (the yield based n the pivaloyl chloride) was 59.89, as shown in the following Table 1.

TABLE 1

|  | Magnesium chloride (mol eq.)[1] | Yield (%) of methyl pivaloylacetate |
|---|---|---|
| Ex. 1 | 0.2 | 70.9 |
| Ex. 2 | 0.5 | 65.8 |
| Comp. Ex. 1 | 1.0 | 59.8 |

[1])Mole equivalent number of anhydrous magnesium chloride to pivaloyl chloride.

The results given in Table 1 indicate that the target. methyl pivaloylacetate could be obtained at higher yields in Examples 1 and 2, where the reaction between pivaloyl chloride and methyl acetoacetate was performed in the presence of pyridine and 0.2 or 0.5 mol equivalent of magnesium chloride based on pivaloyl chloride, than in Comparative Example 1 where the reaction between pivaloyl chloride and methyl acetoacetate was performed in the presence of pyridine and 1.0 mol equivalent (i.e., in the equimolar amount) of magnesium chloride to pivaloyl chloride.

Example 3

(1) 72.2 g (0.622 mol) of methyl acetoacetate and 7.90 g (83.0 mmol) of anhydrous magnesium chloride were suspended in 200 ml of toluene. Into the suspension thus obtained, 96.5 g (1.04 mol) of 2-picoline was dropped at 0° C. After stirring for 10 minutes, 50.0 g (0.415 mmol) of pivaloyl chloride was slowly dropped thereinto at the same temperature and the obtained mixture was reacted under stirring at 40° C. for 10 hours and then at room temperature for 8 hours.

(2) To the reaction mixture obtained in (1), 34.6 g (1.08 mol) of methanol was added and the obtained mixture was stirred at 50° C. for 2.5 hours thereby performing alcoholysis. After cooling the reaction mixture to room temperature, a 259 aqueous solution of sodium carbonate (100 g) was added to the reaction mixture and the reaction mixture was separated into an organic layer and an aqueous layer. After removal of toluene and 2-picoline from the organic layer, the concentrate thus obtained was subjected to vacuum distillation (temperate: 82 to 92° C., pressure: $2.27 \times 10^3$ Pa (17 mmHg)) to give 52.6 g of methyl pivaloylacetate. The yield of the methyl pivaloylacetate based on the pivaloyl chloride serving as the starting material was 80.2%.

Example 4

(1) 81.0 g (0.622 mmol) of ethyl acetoacetate and 7.90 g (83.0 mmol) of anhydrous magnesium chloride were suspended in 200 ml of toluene. Into the suspension thus obtained, 96.5 g (1.04 mol) of α-picoline was dropped at 0° C. After stirring for 10 minutes, 50.0 g (0.415 mmol) of pivaloyl chloride was slowly dropped thereinto at the same temperature and the obtained mixture was reacted under stirring at 60° C. for 7 hours (2) To the reaction mixture obtained:in (1), 49.6 g (1.08 mol) of ethanol was added and the obtained mixture was stirred at 50 to 60° C. for 6.0 hours thereby performing alcoholysis. After thus forming ethyl pivaloylacetate, the reaction mixture was cooled to room temperature.

(3) 100 g of a 259 aqueous solution of sodium carbonate was added to the reaction mixture obtained in (2) and the reaction mixture was separated into an organic layer and an aqueous layer. After distilling off toluene and α-picoline from the organic layer, the concentrate thus obtained was subjected to vacuum distillation (temperature: 80 to 82° C., pressure: $1.60 \times 10^3$ Pa (12 mmHg)) to give 43.3 g of ethyl pivaloylacetate. The yield of the ethyl pivaloylacetate based on the pivaloyl chloride serving as the starting material was 66.1%.

Example 5

(1) 2.32 g (20.0 mmol) of methyl acetoacetate and 737 mg (4.00 mmol) of anhydrous magnesium bromide were suspended in 20 ml of methylene chloride. Into the suspension thus obtained, 3.24 ml (40.0 mmol) of pyridine was dropped at 0° C. After stirring for 10 minutes, 2.46 ml (20.0 mol) of pivaloyl chloride was slowly dropped thereinto at the same temperature and the obtained mixture was reacted under stirring at 0° C. for 15 minutes and then at room temperature for 23 hours.

(2) To the reaction mixture obtained in (1), 1.28 g (40.0 mmol) of methanol was added and the obtained mixture was stirred at room temperature for 3 days thereby performing alcoholysis. After adding 1.50 g of heptadecane (an internal standard), the yield of the methyl pivaloylacetate thus formed was measured by gas chromatography. As a result, the yield of the methyl pivaloylacetate based on the pivaloyl chloride serving as the starting material was 61.7%.

Example 6

(1) 2.32 g (20.0 mmol) of methyl acetoacetate and 233 mg (4.00 mmol) of anhydrous magnesium hydroxide were suspended in 20 ml of methylene chloride. Into the suspension thus obtained, 3.88 ml (48.0 Gel) of pyridine was dropped at 0° C. After stirring for 10 minutes, 3.45 mg (28.0 mmol) of pivaloyl chloride was slowly dropped thereinto at the same temperature and the obtained mixture was reacted under stirring at 0° C. for 15 minutes and then at room temperature for 44 hours.

(2) To the reaction mixture obtained in (1), 1.28 g (40.0 mmol) of methanol was added and the obtained mixture was stirred at room temperature for 3 days thereby performing alcoholysis. After adding 1.50 g of heptadecane (an internal standard), the yield of the methyl pivaloylacetate thus formed was measured by gas chromatography. As a result, the yield of the methyl pivaloylacetate based on the pivaloyl chloride serving as the starting material was 47.5%.

Example 7

(1) 2.60 g (20.0 mmol) of ethyl acetoacetate and 458 mg (4.00 mmol) of anhydrous magnesium ethoxide were suspended in 20 ml of methylene chloride. Into the suspension thus obtained, 3.88 ml (48.0 mmol) of pyridine was dropped at 0° C. After stirring for 10 minutes, 3.45 mg (28.0 mol) of pivaloyl chloride was slowly dropped thereinto at the same temperature and the obtained mixture was reacted under stirring at 0° C. for 15 minutes and then at room temperature for 44 hours.

(2) To the reaction mixture obtained in (1), 1.84 g (40.0 mmol) of ethanol was added and the obtained mixture was stirred at room temperature for 3 days thereby performing alcoholysis. After adding 1.50 g of heptadecane (an internal standard), the yield of the ethyl pivaloylacetate thus formed was measured by gas chromatography. As a result, the yield of the ethyl pivaloylacetate based on the ethyl acetoacetate serving as the starting material was 55.2%.

Example 8

(1) 2.32 g (20.0 mmol) of methyl acetoacetate and 890 mg (4.00 mmol) of anhydrous magnesium acetylacetonate were suspended in 20 ml of methylene chloride. Into the suspension thus obtained, 3.24 ml (40.0 mmol) of pyridine was dropped at 0° C. After stirring for 10 minutes, 2.46 ml (20.0 mmol) of pivaloyl chloride was slowly dropped thereinto at the same temperature and the obtained mixture was reacted under stirring at 0° C. for 15 minutes and then at room temperature for 23 hours.

(2) To the reaction mixture obtained in (1), 1.28 g (40.0 mmol) of methanol was added and the obtained mixture was stirred at room temperature for 3 days thereby performing alcoholysis. After adding 1.50 g of heptadecane (an internal standard), the yield of the methyl pivaloylacetate thus formed was measured by gas chromatography. As a result, the yield of the methyl pivaloylacetate based on the pivaloyl chloride serving as the starting material was 42.7%.

Example 9

(1) 2.32 g (20.0 mmol) of methyl acetoacetate and 381 mg (4.00 mmol) of anhydrous magnesium chloride were suspended in 20 ml of methylene chloride. Into the suspension thus obtained, 4.66 ml (40.0 mmol) of 2,6-lutidine was dropped at 0° C. After stirring for 10 minutes, 2.46 ml (20.0 mmol) of pivaloyl chloride was slowly dropped thereinto at the same temperature and the obtained mixture was reacted under stirring at 0° C. for 15 minutes and then at room temperature for 16 hours.

(2) To the reaction mixture obtained in (1), 1.28 g (40.0 mmol) of methanol was added and the obtained mixture was stirred at room temperature for 3 days thereby performing alcoholysis. After adding 1.50 g of heptadecane (an internal standard), the yield of the methyl pivaloylacetate thus formed was measured by gas chromatography. As a result, the yield of the methyl pivaloylacetate based on the pivaloyl chloride serving as the starting material was 66.5%.

Examples 10 to 15 and Comparative Examples 2 and 3

Methyl pivaloylacetate was produced as in Example 9 but substituting 40.0 mmol of 2,6-lutidine employed in Example 9 by 40.0 mmol of β-picoline (Example 10), γ-picoline (Example 11), dismethylaniline (Example 12), imidazole (Example 13), 1-methylimidazole (Example 14), quinoline (Example 15), triethylamine (Comparative Example 2) or diisopropylethylamine (Comparative Example 3). Table 2 shows the yields of methyl pivaloylacetate based on the pivaloyl chloride serving as the starting material.

TABLE 2

|  | Nitrogen-containing basic compound | Yield (%) of methyl pivaloylacetate |
| --- | --- | --- |
| Ex. 10 | β-picoline | 52.8 |
| Ex. 11 | γ-picoline | 41.5 |
| Ex. 12 | N,N-dimethylaniline | 57.9 |
| Ex. 13 | imidazole | 54.1 |
| Ex. 14 | 1-methylimidazole | 54.1 |
| Ex. 15 | quinoline | 52.5 |
| Comp. Ex. 2 | triethylamine | 2.4 |
| Comp. Ex. 3 | diisopropylethylamine | 1.1 |

The results in the above Table 2 indicate that methyl pivaloylacetate could be obtained at higher yields in Examples 10 to 15, where pyexdine compounds, an N,N-dialkylaniline-dialkylaniline, imidazole, 1-methylimidazole or quinoline were used as the nitrogen-containing basic compound in the reaction between pivaloyl chloride and methyl acetoacetate, than in Comparative Examples 2 and 3 where aliphatic trialkylamines were employed.

Example 16

(1) 4.64 g (40.0 mmol) of methyl acetoacetate and anhydrous magnesium chloride in respective amounts as listed in the following Table 3 were suspended in 40 ml of toluene. Into each suspension thus obtained, 6.47 ml (80.0 mol) of pyridine was dropped at 0° C. After stirring for 10 minutes, 4.93 ml (40.0 mmol) of pivaloyl chloride was slowly dropped thereinto at the same temperature and the obtained mixture was reacted under stirring at 0° C. for 15 minutes and then at room temperature for 16 hours.

(2) To the reaction mixture obtained in (1), 2.56 g (80.0 mmol) of methanol was added and the obtained mixture was stirred at room temperature for 3 days thereby performing alcoholysis. After adding 1.50 g of heptadecane (an internal standard), the yield of the methyl pivaloylacetate thus formed was measured by gas chromatography. As a result, the yields of the methyl pivaloylacetate based on the pivaloyl chloride serving as the starting material were as given in Table 3.

TABLE 3

| Test No. | Anhydrous magnesium chloride | | Yield (%) of methyl pivaloylacetate |
| --- | --- | --- | --- |
| | Used (mmol) | Mol eq.[1] | |
| (i) | 0.8 | 0.02 | 26.6 |
| (ii) | 2 | 0.05 | 38.3 |
| (iii) | 4 | 0.1 | 51.1 |
| (iv) | 8 | 0.2 | 60.4 |
| (v) | 20 | 0.5 | 68.8 |

[1]Mole equivalent number to pivaloyl chloride.

Example 17

(1) 4.64 g (40.0 mmol) of methyl acetoacetate and 762 mg (8.00 mmol) of anhydrous magnesium chloride were suspended in 40 ml of toluene. Into the suspension thus obtained, 7.90 ml (80.0 mmol) of α-picoline was dropped at 0° C. After stirring for 10 minutes, 4.93 ml (40.0 mmol) of pivaloyl chloride was slowly dropped thereinto at the same temperature and the obtained mixture was reacted under stirring at 0° C. for 15 minutes and then at the respective temperatures as listed in the following Table 4 for 16 hours.

(2) To each reaction mixture obtained in (1), 2.56 g (80.0 mmol) of methanol was added and the obtained mixture was stirred at room temperature for 3 days thereby performing alcoholysis. After adding 1.50 g of heptadecane (an internal standard), the yield of the methyl pivaloylacetate thus formed was measured by gas chromatography. As a result, the yields of the methyl pivaloylacetate based on the pivaloyl chloride serving as the starting material were as given in Table 4.

TABLE 4

| Test No. | Reaction temp.[1] (° C.) | Yield (%) of methyl pivaloylacetate |
| --- | --- | --- |
| (i) | 40 | 66.6 |
| (ii) | 50 | 67.6 |
| (iii) | 60 | 65.2 |
| (iv) | 70 | 64.2 |
| (v) | 80 | 63.0 |
| (vi) | 90 | 56.8 |

[1]Reaction temperature in producing ethyl pivaloylacetate.

Example 18

(1) 4.64 g (40.0 mmol) of methyl acetoacetate and 762 mg (8.00 mmol) of anhydrous magnesium chloride were suspended in 40 ml of toluene. Into the suspension thus obtained, 9.88 ml (100 mmol) of α-picoline was dropped at 0° C. After stirring for 10 minutes, 7.40 ml (60.0 mmol) of pivaloyl chloride was slowly dropped there into at the same temperature and the obtained mixture was reacted under stirring at 50° C. for 21 hours.

(2) To the reaction mixture obtained in (1), 3.84 g (120 mmol) of methanol was added and the obtained mixture was stirred at 50° C. for 5 hours thereby performing alcoholysis. After adding 1.50 g of heptadecane (an internal standard), the yield of the methyl pivaloylacetate thus formed was measured by gas chromatography. As a result, the yields of the methyl pivaloylacetate based on the methyl acetoacetate serving as the starting material was 78.6%.

Example 19

(1) 4.64 g (40.0 mmol) of methyl acetoacetate and 762 mg (8.00 mmol) of anhydrous magnesium chloride were suspended in 40 ml of toluene. Into the suspension thus obtained, α-picoline in the respective amounts as listed in the following Table 5 was dropped at 0° C. After stirring for 10 minutes, pivaloyl chloride in the respective amounts as listed in the following Table 5 was slowly dropped thereinto at the same temperature and each mixture thus obtained was reacted under stirring at 50° C. for 16 hours.

(2) To each reaction mixture obtained in (1), 3.84 g (120 mmol) of methanol was added and the obtained mixture was stirred at 50° C. for 5 hours thereby performing alcoholysis. After adding 1.50 g of heptadecane (an internal standard), the yield of the methyl pivaloylacetate thus formed was measured by gas chromatography. As a result, the yields of the methyl pivaloylacetate based on the methyl acetoacetate serving as the starting material were as given in Table 5.

TABLE 5

| Test No. | Pivaloyl chloride employed (mmol) | α-Picoline employed (mmol) | Yield (%) of methyl pivaloylacetate |
|---|---|---|---|
| (i) | 40 | 80 | 67.6 |
| (ii) | 44 | 84 | 70.7 |
| (iii) | 48 | 88 | 73.7 |
| (iv) | 52 | 92 | 75.2 |
| (v) | 56 | 96 | 76.6 |

Example 20

(1) 6.96 g (60.0 mmol) of methyl acetoacetate and 762 mg (8.00 mmol) of anhydrous magnesium chloride were suspended in 40 ml of toluene. Into the suspension thus obtained, 9.88 ml (100 mmol) of α-picoline was dropped at 0° C. After stirring for 10 minutes, 4.93 ml (40.0 mmol) of pivaloyl chloride was slowly dropped thereinto at the same temperature and the mixture thus obtained was reacted under stirring at 50° C. for 21 hours.

(2) To the reaction mixture obtained in (1), 3.84 g (120 mmol) of methanol was aced and the obtained mixture was stirred at 50° C. for 5 hours thereby performing alcoholysis. After adding 1.50 g of heptadecane (an internal standard), the yield of the methyl pivaloylacetate thus formed was measured by gas chromatography. As a result, the yield of the methyl pivaloylacetate based on the pivaloyl chloride serving as the starting material was 76.6%.

Example 21

(1) Methyl acetoacetate in the respective amounts as listed in the following Table 6 and 762 mg (8.00 mmol) of anhydrous magnesium chloride were suspended in 40 ml of toluene. Into the suspensions thus obtained, α-picoline in the respective amounts as listed in the following Table 6 was dropped at 0° C. After stirring for 10 minutes, 4.93 ml (40.0 mmol) of pivaloyl chloride was slowly dropped thereinto at the same temperature and each mixture thus obtained was reacted under stirring at 50° C. for 16 hours.

(2) To each reaction mixture obtained in (1), 3.84 g (120 mmol) of methanol was added and the obtained mixture was stirred at 50° C. for 5 hours thereby performing alcoholysis. After adding 1.50 g of heptadecane (an internal standard), the yield of the methyl pivaloylacetate thus formed was measured by gas chromatography. As a result, the yields of the methyl pivaloylacetate based on the pivaloyl chloride serving as the starting material were as given in Table 6.

TABLE 6

| Test No. | Methyl acetoacetate employed (mmol) | α-Picoline employed (mmol) | Yield (%) of methyl pivaloylacetate |
|---|---|---|---|
| (i) | 40 | 80 | 67.6 |
| (ii) | 44 | 84 | 69.9 |
| (iii) | 48 | 88 | 74.5 |
| (iv) | 52 | 92 | 74.5 |
| (v) | 56 | 96 | 75.3 |

Example 22

(1) 48.2 g (0.415 mmol) of methyl acetoacetate and 7.90 g (83.0 mol) of anhydrous magnesium chloride were suspended in 200 ml of toluene. Into the suspension thus obtained, 65.7 g (0.830 mol) of pyridine was dropped at 0° C. After stirring for 10 minutes, 50.0 g (0.415 mmol) of pivaloyl chloride was slowly dropped thereinto at the same temperature and the obtained mixture was reacted under stirring at room temperature for 16 hours.

(2) To the reaction mixture obtained in (1), 34.6 g (1.08 mol) of methanol was added and the obtained mixture was stirred at 50° C. for 2.5 hours thereby performing alcoholysis. Then the reaction mixture was cooled to room temperature.

(3) 100 g of a 25% aqueous solution of sodium carbonate was added to the reaction mixture obtained in (2) and the reaction mixture was separated into an organic layer and an aqueous layer. After distilling off toluene and pyridine from the organic layer, the concentrate thus obtained was subjected to vacuum distillation (temperature; 82 to 92° C., pressure: $2.27 \times 10^3$ Pa (17 mmHg)) to give 42.6 g of methyl pivaloylacetate. The yield of the methyl pivaloylacetate based on the pivaloyl chloride serving as the starting material was 65.0%, as shown in the following Table 7.

Examples 23 and 24

Methyl pivaloylacetate was produced as in Example 22 but altering the organic solvent and the reaction time employed in Example 22 as listed in the following Table 7. Table 7 shows the yields of methyl pivaloylacetate based on the pivaloyl chloride serving as the starting material.

TABLE 7

| | Organic solvent | Reaction time (hours) | Yield (%) of methyl pivaloylacetate |
|---|---|---|---|
| Ex. 22 | toluene | 16 | 76.8 |
| Ex. 23 | tetrahydrofuran | 16 | 48.6 |
| Ex. 24 | methyl ethyl ketone | 17 | 52.8 |

Example 25

(1) A seal stirrer, a Dimroth condenser and a water bath were attached to a four-necked flask (2 liter). Under a nitrogen gas stream, 480 ml of toluene was introduced into the flask followed by 19.04 g (0.200 mol) of anhydrous magnesium chloride and 174.18 g (1.50 mol) of methyl acetoacetate. Then 204.89 g (2.20 mol) of α-picoline was dropped from a dropping funnel thereinto at 50° C. Subsequently, 120.58 g (1.00 mol) of pivaloyl chloride was dropped from a dropping funnel thereinto at 50 to 60° C. and the mixture was reacted at 60 to 70° C. for 5 hours.

(2) The reaction mixture obtained in (1) was cooled to 40° C. and then 254.4 g of a 25% aqueous solution of soda ash was added thereto. After stirring for 30 minutes, the mixture was allowed to stand and thus separated into an organic layer and an aqueous layer.

(3) After recovering the organic layer, α-picoline and toluene were distilled off under reduced pressure with the use of a Claisen distillation apparatus to thereby give a concentrate containing methyl pivaloylacetoacetate.

(4) 240 ml of methanol was added to the concentrate obtained in (3) and the resultant mixture was stirred under reflux for 3 hours thereby performing alcoholysis. After the recovery of methanol and crude distillation, precise distillation was carried out. Thus 96.76 g of methyl pivaloylacetate having a purity measured by gas chromatography of 99.9% was obtained. The yield of the methyl pivaloylacetate based on the pivaloyl chloride serving as the starting material was 60.1%.

By using the process according to the invention, a pivaloylacetic acid ester, which has a high purity and is little contaminated with by-products and therefore efficiently usable as, for example, a starting material in producing a yellow coupler to be used as a photographic photosensitive material, can be smoothly produced.

By using the process according to the invention, furthermore a magnesium compound is used only in a small amount (i.e., from 0.01 to 0.5 mole equivalent based on pivaloyl chloride). Therefore, the magnesium compound can be easily dispersed in a reaction medium and favorable operating characteristics (for example, stirring) are achieved during the reaction.

Since a magnesium compound is used only in a small amount in the process of the invention as described above, moreover, only a small amount of the magnesium compound is discharged as a waste after the completion of the reaction. Thus, the waste can be easily treated, which is desirable from the viewpoint of preventing environmental pollution.

In addition, a relatively expensive magnesium compound (for example, anhydrous magnesium chloride) is employed only in a small amount in the process of the invention, which contributes to the cost reduction in producing the pivaloylacetic acid ester.

Furthermore, a highly pure pivaloylacetic acid ester can be produced at an extremely high yield by using at least one of anhydrous magnesium chloride and anhydrous magnesium bromide, particularly anhydrous magnesium chloride as the magnesium compound and α-picoline, pyridine or 2,6-lutidine (in particular, α-picoline) as the nitrogen-containing basic compound (a) in the process of the invention.

While the invention has been described in detail and with reference to specific embodiments thereof, it will be apparent to one skilled in the art that various changes and modifications can be made therein without departing from the spirit and scope thereof.

This application is based on Japanese patent application No. 2000-5144 filed on Jan. 14, 2000, the entire contents of which incorporated herein by reference.

What is claimed is:

1. A process for producing a pivaloylacetic acid ester which comprises reacting pivaloyl chloride represented by the following chemical formula (I):

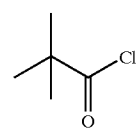

(I)

with an acetoacetic acid ester represented by the following general formula (II):

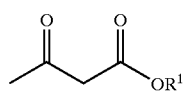

(II)

wherein $R^1$ represents an alkyl group having 1 to 4 carbon atoms; in the presence of at least one nitrogen-containing basic compound (a) selected from the group consisting of pyridine compounds, N,N-dialkylanilines and imidazole compounds and from 0.01 to 0.5 mole equivalent, based on the pivaloyl chloride, of a magnesium compound (b) to thereby prepare a pivaloylacetoacetic acid ester represented by the following general formula (III):

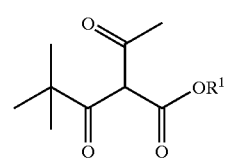

(III)

wherein $R^1$ represents an alkyl group having 1 to 4 carbon atoms; and then alcoholyzing or alkali-hydrolyzing the pivaloylacetoacetic acid ester to thereby give a pivaloylacetic acid ester represented by the following general formula (IV):

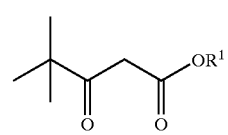

(IV)

wherein $R^1$ represents an alkyl group having 1 to 4 carbon atoms.

2. The process for producing a pivaloylacetic acid ester as claimed in claim 1, wherein said magnesium compound (b) is at least one anhydrous magnesium compound selected from the group consisting of anhydrous magnesium chloride, anhydrous magnesium bromide, anhydrous magnesium hydroxide, anhydrous magnesium alkoxides and anhydrous magnesium acetylacetonate.

3. The process for producing a pivaloylacetic acid ester as claimed in claim 1, wherein said magnesium compound (b) is anhydrous magnesium chloride and/or anhydrous magnesium bromide.

4. The process for producing a pivaloylacetic acid ester as claimed in claim 1, wherein said pyridine compound is pyridine or a pyridine derivative represented by the following general formula (V):

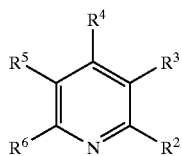 (V)

wherein $R^2$, $R^3$, $R^4$, $R^5$ and $R^6$ each independently represents a hydrogen atom, a methyl group or an ethyl group, or $R^2$ and $R^3$ or $R^3$ and $R^4$ may be bonded to each other to form a ring; and said N,N-dialkylaniline is N,N-dimethylaniline, N,N-diethylaniline or N-methyl-N-ethylaniline.

5. The process for producing a pivaloylacetic acid ester as claimed in claim 1, wherein said nitrogen-containing basic compound (a) is at least one nitrogen-containing basic compound selected from the group consisting of α-picoline, pyridine and 2,6-lutidine.

6. The process for producing a pivaloylacetic acid ester as claimed in claim 1, wherein the reaction for producing a pivaloylacetoacetic acid eater represented by the general formula (III) is performed at a temperature of 0 to 100° C.

7. The process for producing a pivaloylacetic acid ester as claimed in claim 1, wherein said magnesium compound (b) is anhydrous magnesium chloride and/or anhydrous magnesium bromide, and said nitrogen-containing basic compound (a) is at least one nitrogen-containing basic compound selected from the group consisting of α-picoline, pyridine and 2,6-lutidine.

* * * * *

UNITED STATES PATENT AND TRADEMARK OFFICE
CERTIFICATE OF CORRECTION

PATENT NO. : 6,570,035 B2
DATED : May 27, 2003
INVENTOR(S) : Shinya Yamada et al.

It is certified that error appears in the above-identified patent and that said Letters Patent is hereby corrected as shown below:

Title page,
Item [56], References Cited, FOREIGN PATENT DOCUMENTS, insert
-- EP 481395 A   4/92   C07C   67/333 --.

Signed and Sealed this

Twentieth Day of July, 2004

JON W. DUDAS
*Acting Director of the United States Patent and Trademark Office*